(12) United States Patent
Samuelson et al.

(10) Patent No.: US 7,052,897 B2
(45) Date of Patent: May 30, 2006

(54) ALTERATION OF RESTRICTION ENDONUCLEASE SPECIFICITY BY GENETIC SELECTION

(75) Inventors: James C. Samuelson, Newburyport, MA (US); Shuang-yong Xu, Lexington, MA (US)

(73) Assignee: New England Biolabs, Ipswich, MA (US)

(*) Notice: Subject to any disclaimer, the term of this patent is extended or adjusted under 35 U.S.C. 154(b) by 124 days.

(21) Appl. No.: 10/501,196

(22) PCT Filed: Jan. 9, 2003

(86) PCT No.: PCT/US03/00542

§ 371 (c)(1),
(2), (4) Date: Jul. 9, 2004

(87) PCT Pub. No.: WO03/060152

PCT Pub. Date: Jul. 24, 2003

(65) Prior Publication Data

US 2005/0164186 A1 Jul. 28, 2005

Related U.S. Application Data

(60) Provisional application No. 60/347,403, filed on Jan. 10, 2002.

(51) Int. Cl.
*C12N 9/22* (2006.01)
*C12N 9/10* (2006.01)

(52) U.S. Cl. ........................................ 435/199; 435/193

(58) Field of Classification Search ................ 435/199, 435/193, 440, 471
See application file for complete search history.

(56) References Cited

U.S. PATENT DOCUMENTS 5,498,535 A * 3/1996 Fomenkov et al. ............ 435/6
6,893,854 B1 * 5/2005 Janulaitis et al. ........... 435/199

FOREIGN PATENT DOCUMENTS

EP 1 179 596 * 2/2002

OTHER PUBLICATIONS

Samuelson, J.C., et al. (2002) J. Mol. Biol. 319, 673-683.*
Nelson, M., et al. (1984) Nucl. Acids Res. 12(13), 5165-5173.*
Arkin et al. Proc. Natl. Acad. Sci. USA 89:7811-7815 (1992).
Arnold et al. Curr. Opin. Biotechnol. 4:450-455 (1993).

(Continued)

*Primary Examiner*—Charles L. Patterson, Jr.
(74) *Attorney, Agent, or Firm*—Harriet M. Strimpel

(57) ABSTRACT

Methods and compositions are provided for altering the DNA recognition and cleavage characteristics of an endonuclease without prior knowledge of the endonuclease's three-dimensional structure and/or amino acid residues responsible for activity and/or specificity. Methods include subjecting a mutagenized endonuclease gene library to a genetic selection in prokaryotic cells which tolerate the expression of mutated endonuclease and where the endonuclease is active and determining the altered recognition-site specificity for the endonuclease.

17 Claims, 8 Drawing Sheets

OTHER PUBLICATIONS

Bingle et al. Can. J. Microbiol. 39:70-80 (1993).
Cadwell et al. PCR Methods Applic. 2:29-33 (1992).
Delegrave et al. Biotechnology Res. 11:1548-1552 (1993).
Dorner et al. J. Mol. Biol. 285:1515-1523 (1999).
Dorner et al. Nucl. Acids Res. 22:1068-1074 (1994).
Engelrecht et al. Science 227:1345-1347 (1985).
Flores et al. Gene 157:295-301 (1995).
Heitman et al. Proteins 7:185-197 (1990).
Heitman et al. EMBO J. 9:3369-3378 (1990).
Heitman et al. Bioessays 14:445-454 (1992).
Hoffman et al. Proc. Natl. Acad. Sci. USA 82:5107-5111 (1985).
Horton et al. J. Biol. Chem. 273:21721-21729 (1998).
Ivanenko et al. Biol. Chem. 379:459-465 (1998).
Iwasaki et al. J. Bacteriol. 172:6268-6273 (1990).
Lanio et al. Protein Eng. 13:275-281 (2000).
Lanio et al. J. Mol. Biol. 283:59-69 (1998).
Leung et al. Technique 1:11-15 (1989).
Lewis et al. J. Bacteriol. 174:3377-3385 (1992).
Long-McGie et al. Biotechnol. Bioeng. 68:121-125 (2000).
Metcalfe et al. Gene 129:17-25 (1993).
Morrison et al. Biotechniques 14:454-457 (1993).
Muir et al. J. Mol. Biol. 274:722-737 (1997).
Newman et al. Science 269:5656-663 (1995).
Newman et al. Nature 368:660-664 (1994).
Pingoud et al. Nucl. Acids Res. 29:3705-3727 (2001).
Roberts et al. Nucl. Acids Res. 29:268-269 (2001).
Stemmer et al. Proc. Natl. Acad. Sci. USA 91:10747-10751 (1994).
Thompson et al. Nucl. Acids Res. 16:9687-9705 (1988).
Ward et al. Mol. Gen. Genet. 203:468-478 (1986).
Whitaker et al. J. Mol. Biol. 285:1525-1536 (1999).
Xu et al. J. Biol. Chem. 266:4425-4429 (1991).

* cited by examiner

**Genetic Selection of *Bst*YI Variants with 5'-AGATCT-3' specificity**

FIGURE 2

```
      ATGAGAATTGTTGAAGTATATTCGCATTTGAACGGGTTGGAATACATACAAGTTCACTTG
  1   ---------+---------+---------+---------+---------+---------+  60
      M  R  I  V  E  V  Y  S  H  L  N  G  L  E  Y  I  Q  V  H  L
      CCACATATTTGGGAAGAAATTCAAGAAATTATTGTTTCTATTGACGCAGAAGCTTGTAGA
 61   ---------+---------+---------+---------+---------+---------+ 120
      P  H  I  W  E  E  I  Q  E  I  I  V  S  I  D  A  E  A  C  R
      ACGAAGGAATCAAAAGAAAAGACAAAACAAGGACAAATACTTTATAGTCCCGTAGCTTTA
121   ---------+---------+---------+---------+---------+---------+ 180
      T  K  E  S  K  E  K  T  K  Q  G  Q  I  L  Y  S  P  V  A  L
      AATGAAGCATTCAAGGAAAAATTAGAAGCAAAAGGTTGGAAAGAAAGTCGAACAAACTAT
181   ---------+---------+---------+---------+---------+---------+ 240
      N  E  A  F  K  E  K  L  E  A  K  G  W  K  E  S  R  T  N  Y
      TATGTGACTGCTGACCCAAAGCTGATTCGTGAAACATTATCACTTGAACCAGAGGAACAA
241   ---------+---------+---------+---------+---------+---------+ 300
      Y  V  T  A  D  P  K  L  I  R  E  T  L  S  L  E  P  E  E  Q
      AAGAAAGTGATTGAAGCCGCAGGAAAAGAAGCATTAAAGTCTTATAATCAAACGGATTTT
301   ---------+---------+---------+---------+---------+---------+ 360
      K  K  V  I  E  A  A  G  K  E  A  L  K  S  Y  N  Q  T  D  F
      GTAAAAGATAGAGTGGCAATAGAAGTTCAATTCGGAAAATATTCTTTTGTCGCTTATGAC
361   ---------+---------+---------+---------+---------+---------+ 420
      V  K  D  R  V  A  I  E  V  Q  F  G  K  Y  S  F  V  A  Y  D
      CTTTTCGTCAAACACATGGCTTTCTATGTTAGTGATAAAATTGACGTTGGTGTCGAAATA
421   ---------+---------+---------+---------+---------+---------+ 480
      L  F  V  K  H  M  A  F  Y  V  S  D  K  I  D  V  G  V  E  I
      TTGCCAATGAAGGAATTATCAAAAGAAATGTCTTCGGGAATCAGTTATTACGAAGGTGAA
481   ---------+---------+---------+---------+---------+---------+ 540
      L  P  M  K  E  L  S  K  E  M  S  S  G  I  S  Y  Y  E  G  E
      TTATACAATGTGATACGGCAAGGTCGTGGCGTTCCTGCCGTTCCGTTGGTTTTAATCGGG
541   ---------+---------+---------+---------+---------+---------+ 600
      L  Y  N  V  I  R  Q  G  R  G  V  P  A  V  P  L  V  L  I  G
      ATTGCCCCTTAA
601   ---------+-- 612
      I  A  P  *
```

5'.....AGATCT.....3'
3'.....TCTAGA.....5'

5'.....GGATCC.....3'
3'.....CCTAGG.....5'

5'.....AGATCC.....3'
3'.....TCTAGG.....5'

ALTERATION OF RESTRICTION ENDONUCLEASE SPECIFICITY BY GENETIC SELECTION

This application is a § 371 application of international application number PCT/US03/00542 filed 9 Jan. 2003, which claims priority from U.S. provisional application Ser. No. 60/347,403 filed 1 Jan. 2002, herein in-corporated by reference.

BACKGROUND OF THE INVENTION

Type II restriction endonucleases are a class of enzymes that occur naturally in bacteria where they serve as host defense systems, functioning to prevent infection by foreign DNA molecules such as bacteriophage and plasmids that would otherwise destroy or parasitize them. In this defense system, foreign DNA is restricted (cleaved) while host DNA is protected due to modification of the recognition sites by a cognate DNA methyltransferase. This relationship with a DNA methylase ensures that the endonuclease maintains an extremely high degree of specificity. In the course of evolution, any variants with non-cognate restriction activity are subject to strong selection pressure in the form of DNA damage encountered by the bacterial cell.

The remarkable substrate specificity of restriction endonucleases has contributed greatly to the biotechnology revolution. Purification of restriction endonucleases from bacteria allows these enzymes to be used in numerous laboratory applications from gene cloning to mutation detection. Type II restriction endonucleases typically recognize a DNA sequence of 4–8 base pairs (bp). Of the greater than 3000 enzymes characterized so far, 228 distinct substrate specificities have been identified. (Roberts and Macelis, *Nucl. Acids Res.* 29:268–269 (2001)). The substrate specificity of a restriction endonuclease usually involves single site recognition (e.g. 5'-AGATCT-3') However, a relatively common feature is recognition of a degenerate sequence. For example, BstYI recognizes 5'-RGATCY-3' (where R=A or G and Y=C or T). Recognition of a degenerate sequence often limits the utility of a restriction enzyme in laboratory applications since cleavage frequency is excessive. Statistically, an enzyme recognizing a 6-bp sequence cleaves every 4096 bp while an enzyme recognizing 5'-RGATCY-3' cleaves every 1024 bp on average in a non-biased genome. Restriction endonucleases that cut infrequently (e.g. 8-bp cutting enzymes that cleave every 65,536) are rarely found in nature. Therefore, many engineering efforts are focused on creating less frequent cutters out of existing 6-bp cutters.

More than ten years of endonuclease engineering has resulted in only limited success in altering the substrate specificity of an existing restriction endonuclease. One important example is an attempt to engineer an 8-bp cutting enzyme from EcoRV (5'-GATATC-3') by using rational protein design based on the high resolution structures of EcoRV complexed with alternate 8-bp substrates (Horton and Perona, *J. Biol. Chem.* 273:21721–21729 (1998)). In this case, rational protein design pertained to creating one or more specific amino acid substitutions by site-directed mutagenesis of the cloned gene fragment. A conclusion of this effort was that the determinants of altering substrate specificity are difficult to predict even after crystallographic analysis of an endonuclease/DNA substrate complex (Lanio, et al., *Protein Eng.* 13:275–281 (2000)). The most promising EcoRV variant was derived from a semi-rational approach where twenty-two amino acid residues were chosen for randomization based on examination of the three-dimensional structure. Clones of interest were selected by in vitro analysis of cleavage activity and specificity. From this effort, a triple mutant was identified which exhibited a 25-fold higher rate of cleaving EcoRV sites flanked by AT rather than GC base pairs. (Lanio, et al., *J. Mol. Biol.* 283:59–69 (1998)).

Many other studies have been conducted to investigate and possibly alter the substrate specificity of the restriction enzymes BamHI (Dorner and Schildkraut, *Nucl. Acids Res.* 22:1068–1074 (1994), Dorner, et al., *J. Mol. Biol.* 285:1515–1523 (1999), Whitaker, et al., *J. Mol. Biol.* 285:1525–1536 (1999), Newman, et al., *Science* 269:656–663 (1995), Newman, et al., *Nature* 368:660–664 (1994)) and EcoRI (Ivanenko, et al., *J. Biol. Chem.* 379:459–465 (1998), Heitman and Model, *Proteins* 7:185–197 (1990), Heitman, *Bioessays* 14:445–454 (1992), Muir, et al., *J. Mol. Biol.* 274:722–737 (1997), Flores, et al., *Gene* 157:295–301 (1995)). Again, structure-based rational or semi-rational design approaches were employed with no absolute change of specificity reported. To date, a total of twelve structures of restriction enzymes have been determined (Pingoud and Ieltsch, *Nucl. Acids Res.* 29:3705–3727 (2001)). From these structures, it is becoming clear that substrate recognition does not adhere to a distinct set of rules. Consequently, the likelihood of engineering novel substrate specificities into existing endonucleases by purely rational design methods remains low. Furthermore, protein structure determination remains to be a costly and time-consuming endeavor.

Consequently, a rapid and more successful method of endonuclease engineering is required to identify amino acid substitutions responsible for altering substrate specificity without the requirement of protein structural information.

SUMMARY OF THE INVENTION

The present invention provides a novel method for altering the DNA recognition and cleavage specificity of an endonuclease. Prior knowledge of the endonuclease three-dimensional structure and/or knowledge of the amino acids responsible for substrate recognition are not required.

In an embodiment of the invention, a method is provided for altering an endonuclease recognition site specificity, that includes: subjecting a mutagenized endonuclease gene library to a genetic selection in a population of prokaryotic host cells expressing one or more non-cognate DNA methyltransferases, wherein the genetic selection selects for viable cells in the population; and identifying whether the viable cells express an active mutated endonuclease with an altered recognition site specificity.

The mutagenized endonuclease gene library may be formed by: error prone PCR, chemical mutagenesis, assembly PCR, DNA shuffling, in vivo mutagenesis, cassette mutagenesis, recursive-ensemble mutagenesis or exponential ensemble mutagenesis.

The endonuclease activity may be attenuated by modifying the mutagenized endonuclease gene library using modification means selected from: creating an amber codon within the open reading frame; creating an opal codon within the open reading frame; changing the start codon to GTG or TTG; mutating the RBS sequence or utilizing a T7 expression vector wherein the host cell is T7 RNA polymerase negative.

In addition to the above, viable prokaryotic host cells may be pooled and plasmid DNA isolated from the cells where the plasmid DNA encodes mutagenized endonuclease genes from the library and transforming the plasmid DNA into a population of indicator cells for detecting DNA damage. The mutagenized endonuclease genes may be subjected to repeated genetic selections in the population of host cells described above and in the population of indicator cells where the genetic selection in the population of indicator cells includes a first population of indicator cells lacking non-cognate methylase and a second population of indicator cells expressing the non-cognate methylases.

The sequence of the altered recognition site can be determined where the altered specificity for the site may be relaxed recognition-site specificity, increased recognition-site specificity or alternate recognition-site specificity.

In a further embodiment of the invention, a method is provided for altering recognition site specificity of an endonuclease, that includes: creating a mutagenized endonuclease gene expression plasmid library from a target endonuclease gene and transforming prokaryotic cells with the mutagenized library, wherein the prokaryotic cells express one or more non-cognate methyltransferase; selecting prokaryotic cells which are viable after transformation and isolating plasmid DNA from the viable cells; determining whether the isolated plasmid DNA encodes an active endonuclease by transforming the plasmid DNA into DNA damage indicator cells; screening the plasmid DNA encoding the active endonuclease for altered specificity; and optionally repeating the above protocol to obtain the endonuclease with altered recognition-site specificity. An example of the above method is an endonuclease having an altered recognition site derived from BstYI or NotI.

In a further embodiment of the invention, a method is provided for modifying recognition-site specificity of an endonuclease from a parent specificity to a target specificity, that include obtaining a sequence for a plurality of mutated endonucleases obtained by the methods described above to determine the mutation for each mutated endonuclease; and mutating a gene encoding the endonuclease to produce one or more of the mutations identified above so as to provide the target specificity for the endonuclease.

BRIEF DESCRIPTION OF THE DRAWINGS

FIG. 2 is the nucleotide (SEQ ID NO:1) and amino acid sequence (SEQ ID NO:2) of BstYI endonuclease.

FIG. 4 is the DNA cleavage characteristics of clone NN1 vs. wild-type BstYI assayed on radiolabeled DNA substrates (60 bp) each containing one of the three unique BstYI recognition sites.

DETAILED DESCRIPTION OF THE INVENTION

Definitions

Figure 1A:
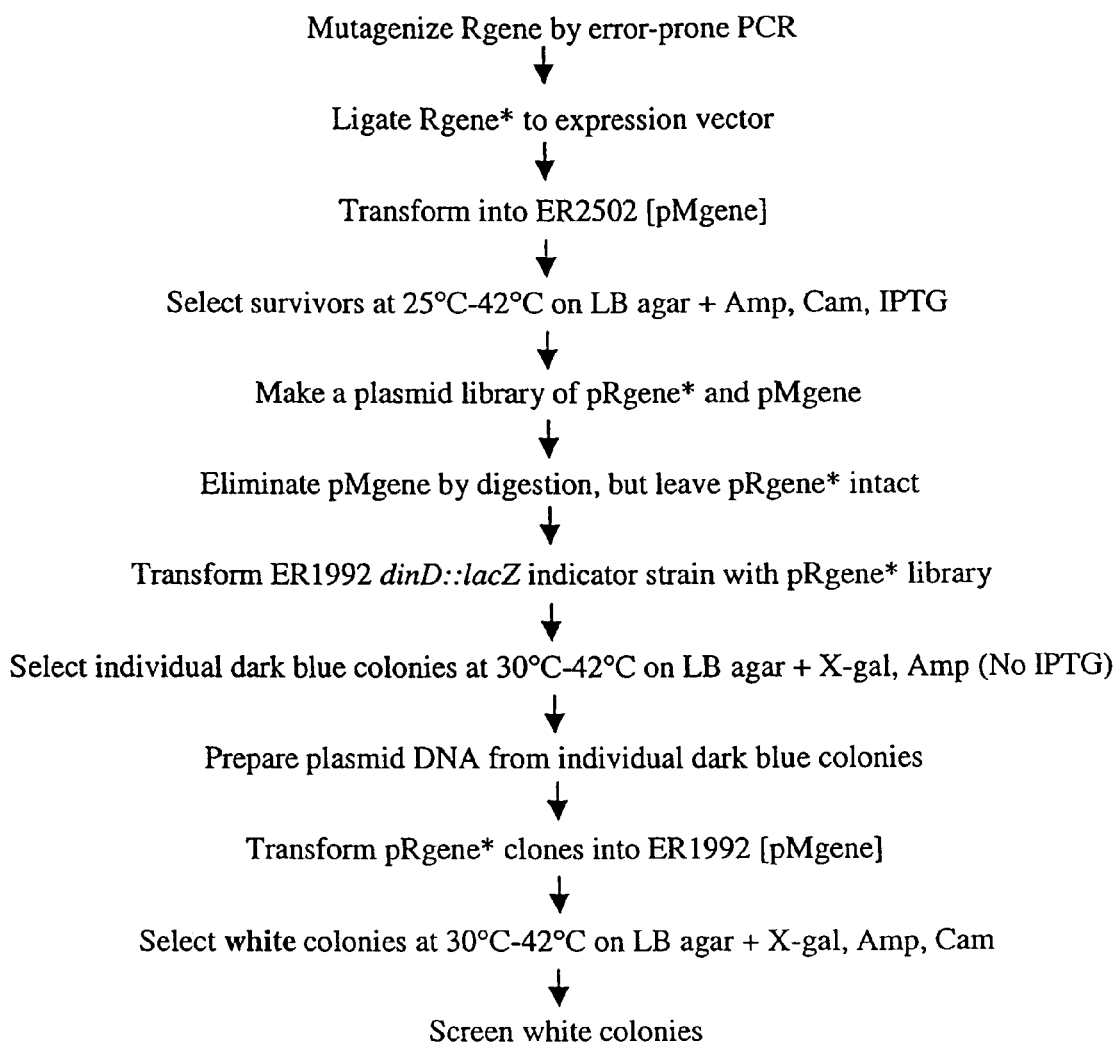
FIG. 1A is an outline of the genetic selection procedure. Rgene*, mutated endonuclease gene library; Mgene, non-cognate DNA methylase gene.

For convenience, certain terms employed in the specification, examples and appended claims are collected here.

"Non-cognate methylase" refers herein to a DNA methyltransferase possessing a substrate specificity that does not protect a target recognition site(s) of a given endonuclease.

"Mutation" refers herein to any gene alteration including DNA rearrangement; nucleotide(s) substitution, addition and/or deletion that results in expression of an endonuclease possessing an altered amino acid sequence.

"Active" refers herein to an endonuclease capable of binding a recognition site(s) or capable of binding and cleaving a recognition site(s). Binding activity may be determined, for example, by an electrophoretic mobility shift assay (Thompson and Landy, *Nucl. Acids Res.* 16:9687–9705 (1988)), filter binding assay (Zhenyu Zhu, New England Biolabs) or may be reported by an indicator strain capable of sensing site-specific DNA binding. Cleavage activity may be determined in vivo by an indicator strain capable of reporting DNA damage or in vitro by incubating cell extract or partially purified endonuclease with an appropriate DNA substrate (Xu and Schildkraut, *J. Biol. Chem.* 266:4425–4429 (1991)).

"Recognition site" refers herein to an uninterrupted or interrupted DNA sequence to which an endonuclease is preferentially bound. DNA cleavage by the endonuclease may occur within or outside of the recognition sequence.

"Tolerated" refers herein to maintenance of cell viability through DNA methylation protection.

"Attenuation" refers herein to intentionally decreasing the in vivo DNA damaging effects of a given endonuclease gene or gene library. Attenuation may occur at the level of transcription, translation, or by alteration of the endonuclease specific activity by mutagenesis.

"Altered specificity" refers herein to any measurable endonuclease activity which differs from the wild-type or parent endonuclease. Altered specificity includes relaxed specificity, increased specificity or alternate specificity.

"Relaxed specificity" refers herein to increased promiscuity of an endonuclease with respect to its recognition site.

"Endonuclease gene library" refers herein to a collection of genes where a majority of the library members are unique with respect to their nucleotide sequence (where a single nucleotide difference between two members qualifies as being unique). The library may be derived from one or more endonuclease gene or each member may be artificially constructed to possess the general characteristics of an endonuclease gene sequence.

In an embodiment of the invention, we provide a method for the genetic selection of endonuclease variants possessing altered substrate specificity as compared to the parent endonuclease. The parent endonuclease may be the product of a wild-type endonuclease gene isolated from nature or the parent endonuclease may itself be a variant isolated by any other means. For example, in the development of an endonuclease possessing an altered recognition site specificity, an important first step may be to isolate a variant with a relaxed specificity. Once the new recognition sites are determined, one or more non-cognate DNA methylases can be employed in vivo to protect the host genomic DNA and thus serve as an enabling factor in the genetic selection procedure of the present invention. The selection of a relaxed specificity variant may be accomplished by transforming a mutagenized endonuclease gene library into a DNA-damage indicator strain protected by a cognate DNA methylase (see example 2 and Heitman and Model, *EMBO J.* 9:3369–3378 (1990)).

In an embodiment of the invention, we subject a mutated endonuclease gene library to a plurality of genetic selections in *E. coli* or other suitable prokaryotic host. While the method may be conducted with a minimum of two genetic selections, three or more selections are preferred to reduce false positives. The procedure yields active variants possessing a high likelihood of having one or more mutations which are either necessary or informative for altering the substrate specificity of the endonuclease. The desired substrate specificity is determined by protecting the host DNA with one or more non-cognate DNA methyltranferase. The host DNA may be methylated at an alternate recognition site(s) to isolate variants with an alternate cleavage preference or the host DNA may be methylated at one or more sub-sites to isolate variants with cleavage preference towards one or more sub-sites.

During the in vivo selection process, host bacterial cells carrying endonuclease variants with DNA cleavage activity outside the spectrum of host DNA methylation are eliminated or at least are strongly selected against due to reduced growth. Therefore, this approach involving laboratory genetic selection steps imposed upon a randomly mutated endonuclease gene may be considered to be analogous to the evolutionary selection process dependent upon native host protection by a cognate DNA methyltransferase.

Figure 1B:
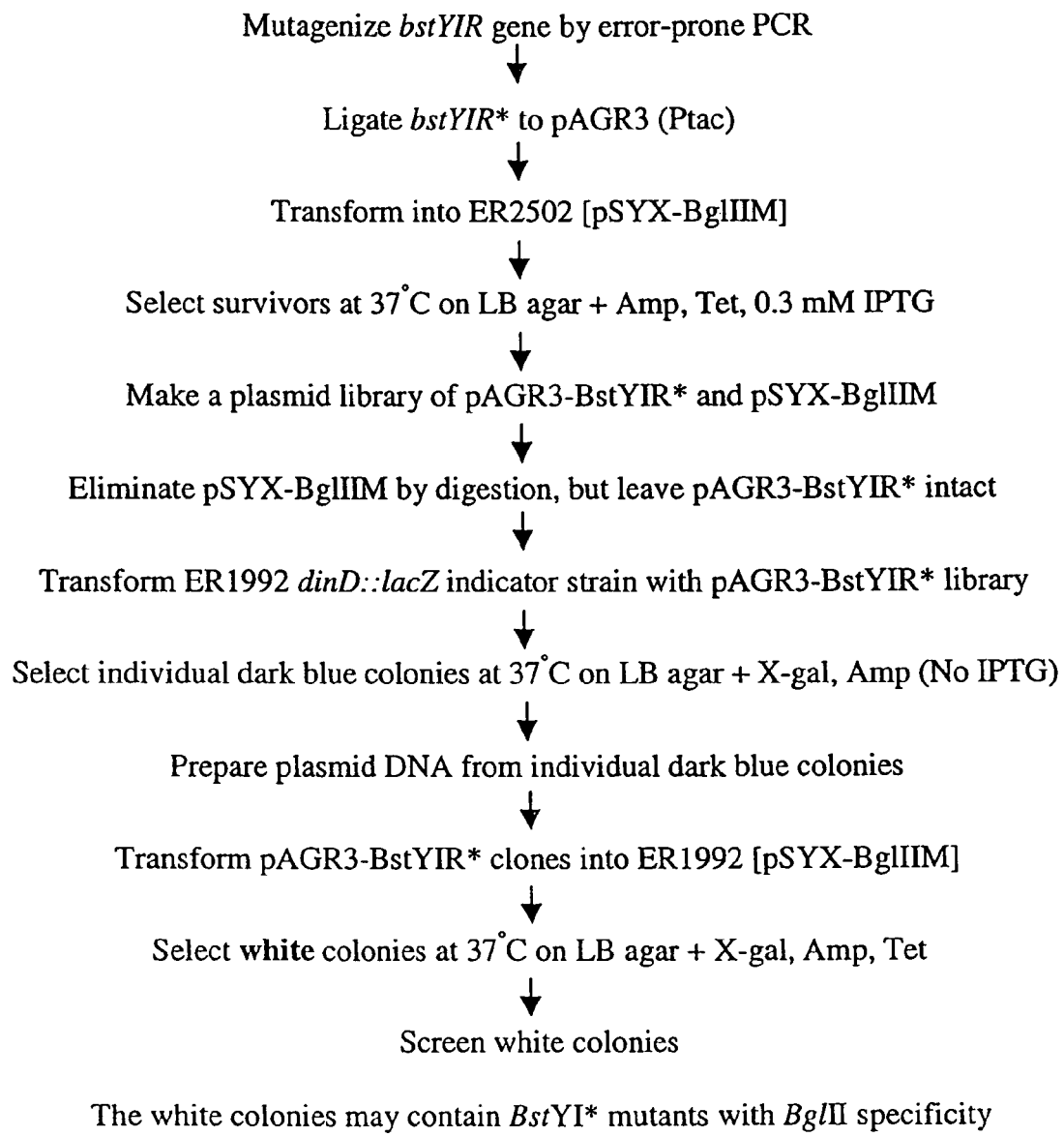
FIG. 1B is an outline of the genetic selection procedure as applied to isolate variants of BstYI with AGATCT specificity.

A protocol we have developed to achieve in vivo selection process (see FIG. 1) includes one or more of the following steps:

(i) generating a mutated endonuclease library within an expression vector or plasmid.

(ii) introducing the endonuclease library into host cells pre-modified with a non-cognate pattern of methylation. The transformed cells are plated on media containing an inducer molecule to maximize elimination of host cells harboring endonuclease variants with DNA cleavage activity outside the spectrum of host DNA methylation.

(iii) pooling survivors and plasmid DNA from the cells. Clones expressing active variants are isolated by transforming the endonuclease plasmids only into an indicator strain for DNA damage, preferably ER1992 (U.S. Pat. No. 5,498, 535). The transformed cells are plated on media void of the inducer molecule to avoid lethal levels of DNA damage, as the indicator strain is not protected by methylation (or only partially protected) in this step. The media does contain the substrate X-gal to allow individual colonies to report significant levels of cellular DNA damage upon induction of the SOS repair response and expression of a dinD1::lacZ gene fusion.

(iv) active endonuclease clones may be isolated by culturing individual dark blue colonies for a short time at a low temperature and preparing plasmid DNA from these cultures. Alternatively, dark blue colonies are pooled and plasmid DNA is prepared without culturing in order to maintain the integrity of active clones.

(v) the individual plasmid isolates (or pooled plasmid DNA) can then be introduced into the DNA damage indicator strain which is pre-modified with the same pattern of methylation as in step (ii). The emergence of white colonies on X-gal media at 37° C. indicates that the endonuclease variant may be exhibiting cleavage preference towards the site(s) protected by methylation.

The methods described herein are effective in altering cleavage specificity of thermophilic restriction enzymes as these enzymes are less active at 30° C.–37° C. and are better tolerated by DNA damage indicator cells not protected by methylation. Yet, endonucleases from mesophilic organisms may be engineered by this method by first attenuating the endonuclease activity and/or expression level as described in Examples 2 and 3 of the present invention.

Figure 4A:
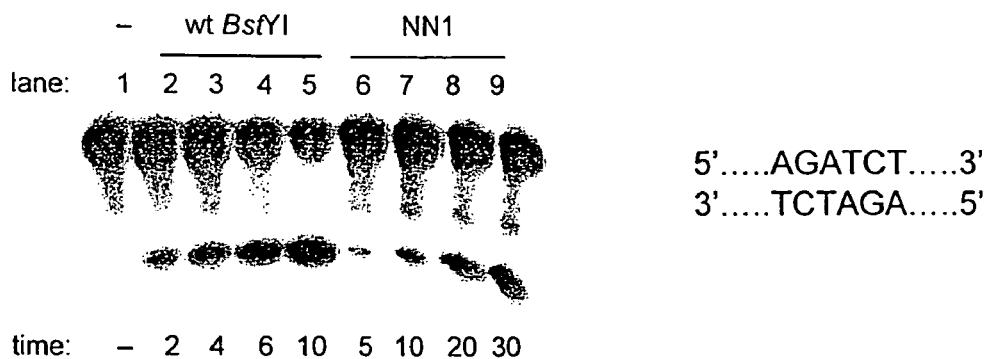
FIG. 4A is cleavage of the 5'-AGATCT-3' site.
Figure 4B:
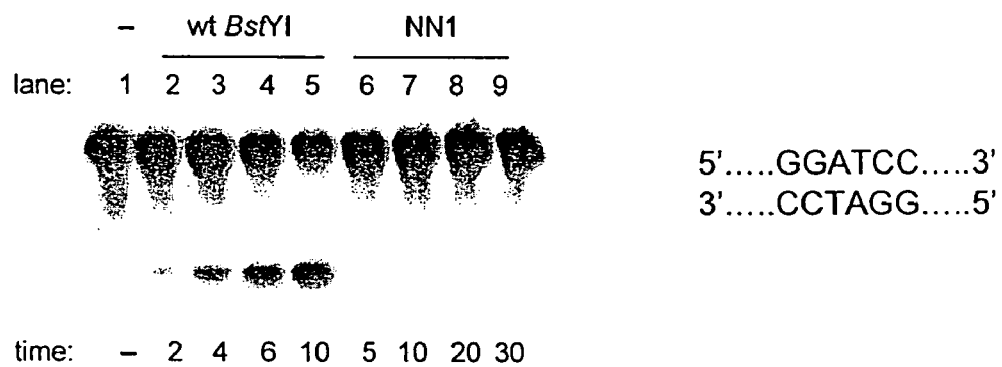
FIG. 4B is cleavage of the 5'-GGATCC site.
Figure 4C:
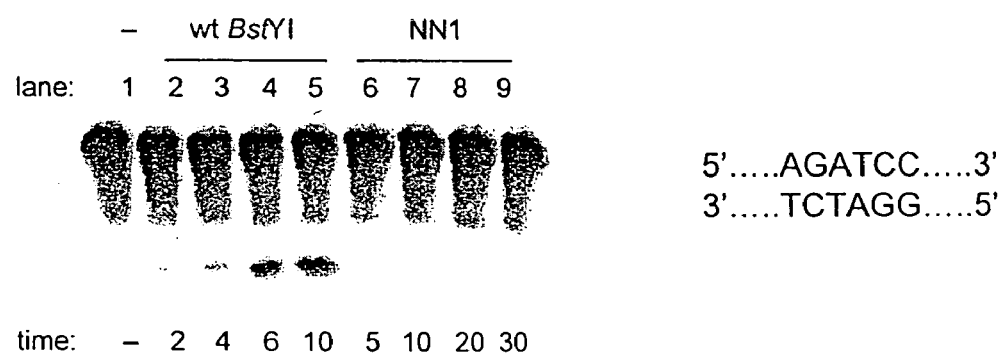
FIG. 4C is cleavage of the 5'-AGATCC-3' site (bottom strand is 5'-GGATCT-3'). In each part, lane 1 is the substrate only. Lanes 2–5 represent cleavage with wild-type BstYI for 2, 4, 6, and 10 min, respectively. Lanes 6–9 represent cleavage with clone NN1 for 5, 10, 20, and 30 min, respectively. All reactions were incubated at 60° C.

We provide examples of a stringent selection method where an estimated $10^7$ variants can be rapidly screened in one round. In Example 1, this was applied to increase the substrate specificity of BstYI (5'-RGATCY-3') to single site recognition (5'-AGATCT-3'). After one round (three selection steps), forty-five clones were analyzed in vitro for activity and specificity. Of those forty-five clones, two variants were found to exhibit a preference for cleavage of 5'-AGATCT-3' over other BstYI sites. By combining single mutations present in each of these clones, a superior clone designated NN1 was isolated. NN1 displays a 7-fold preference for cleavage of 5'-AGATCT-3' relative to 5'-AG-ATCC-3' or 5'-GGATCT-3' and cleavage of the 5'-GGATCC-3' site is not detected (FIG. 4). Embodiments of the inventive method are provided below and comprise the following steps, although as the skilled artisan will appreciate, modifications to these steps may be made without adversely affecting the outcome:

Although not essential, the skilled artisan may choose to consult any available gene homology or protein structural information that pertains to the endonuclease under study or to the appropriate family of endonucleases. This information may be useful in determining and designing the method of mutagenesis.

1) A given endonuclease gene is mutagenized by methods generally known in the art including any of:

(a) Error-prone PCR (Leung, et al., *Technique* 1:11–15 (1989), Cadwell and Joyce, *PCR Methods Applic.*, 2:28–33 (1992)).

(b) Hydroxylamine, sodium bisulfite or any other chemical mutagen treatment. (Sambrook, J., et al., Molecular Cloning: A Laboratory Manual, $2^{nd}$ ed. (1989)).

(c) Oligonucleotide directed mutagenesis, preferably the overlap extension PCR mutagenesis method (Morrison and Desrosiers, *Biotechniques* 14:454–457 (1993)).

(d) Assembly PCR. The term "assembly PCR" refers to a process that involves the assembly of a PCR product from a mixture of small DNA fragments. A large number of different PCR reactions occur in parallel in the same vial, with the products of one reaction priming the products of another reaction.

(e) Sexual PCR mutagenesis. The term "sexual PCR mutagenesis" (also known as "DNA shuffling") refers to forced homologous recombination between DNA molecules of different but highly related DNA sequence in vitro, caused by random fragmentation of the DNA molecule, based on sequence homology, followed by fixation of the crossover by primer extension in a PCR reaction. (Stemmer, *Proc., Natl. Acad. Sci.*, USA 91:10747–10751 (1994)).

(f) In vivo mutagenesis. The term "in vivo mutagenesis" refers to a process of generating random mutations in any cloned DNA of interest which involves the propagation of the DNA in a strain of *E. coli* that carries mutations in one or more of the DNA repair pathways. These mutator strains have a higher random mutation rate than that of a wild-type strain. Propagating the DNA in one of these strains will generate random mutations within the DNA. (Long-McGie, et al., *Biotechnol. Bioeng.* 68:121–125 (2000)).

(g) Cassette mutagenesis. The term "cassette mutagenesis" refers to any process for replacing a small region of a double-stranded DNA molecule with a synthetic oligonucleotide cassette that differs from the native sequence. The oligonucleotide often contains completely or partially randomized native sequence. (Dorner, et al., *J. Mol. Biol.* 285:1515–1523 (1999)).

h) Recursive ensemble mutagenesis. The term "recursive ensemble mutagenesis" refers to an algorithm for protein engineering (protein mutagenesis) developed to produce diverse populations of phenotypically related mutants whose members differ in amino acid sequence. This method uses a feedback mechanism to control successive rounds of combinatorial cassette mutagenesis (Arkin and Youvan, *Proc. Natl. Acad. Sci., USA* 89:7811–7815 (1992)).

(i) Exponential ensemble mutagenesis. The term "exponential ensemble mutagenesis" refers to a process for generating combinatorial libraries with a high percentage of unique and functional mutants, wherein small groups of residues are randomized in parallel to identify, at each altered position, amino acids which lead to functional proteins (Delegrave and Youvan, *Biotechnology Res.* 11:1548–1552 (1993)) and random and site-directed mutagenesis (Arnold, *Curr. Opin. Biotechnol.* 4:450–455 (1993)).

Each of these techniques is described in detail in the cited references herein incorporated by reference.

Figure 6:
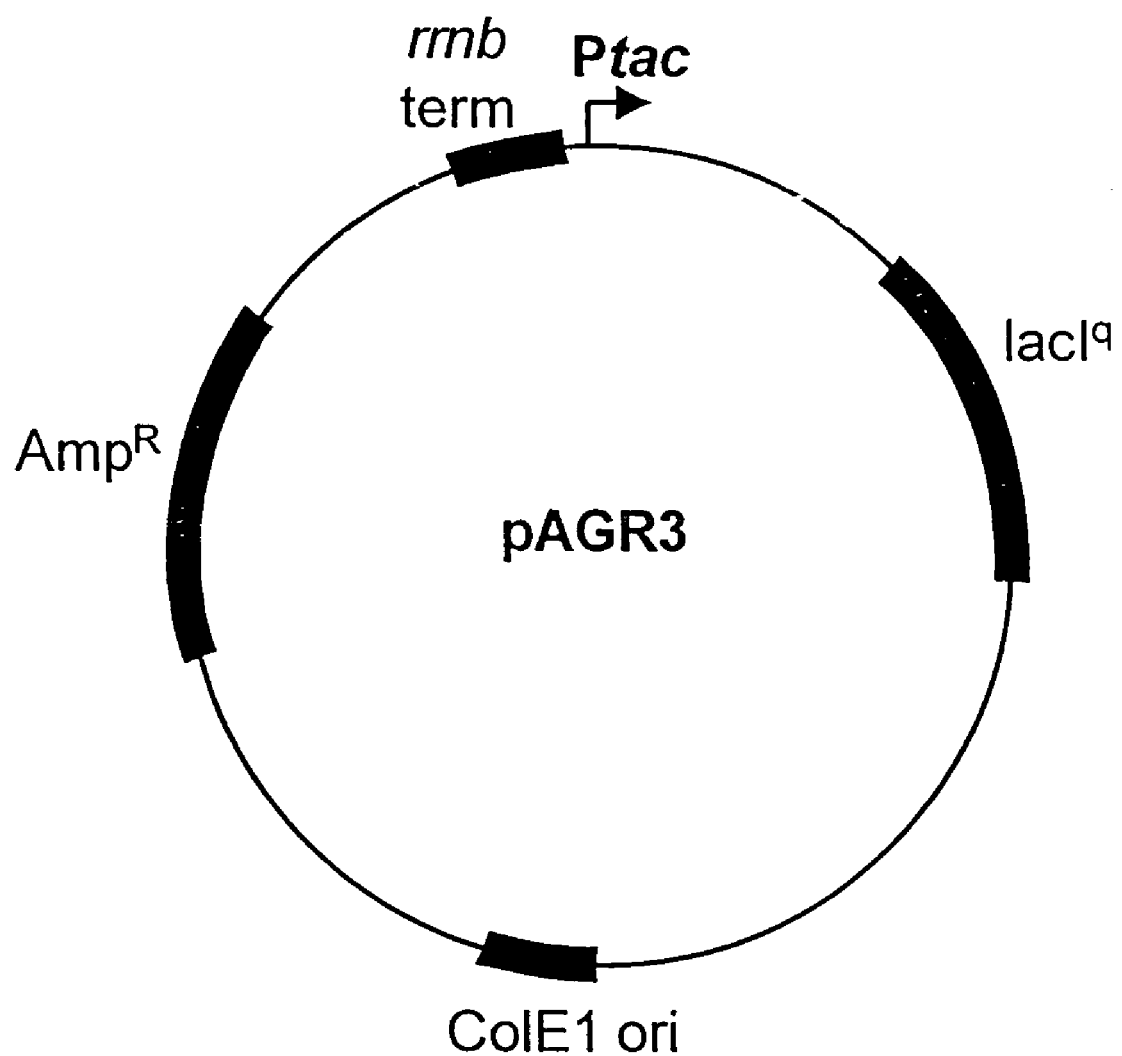
FIG. 6 shows a map of pAGR3.
Figure 7:
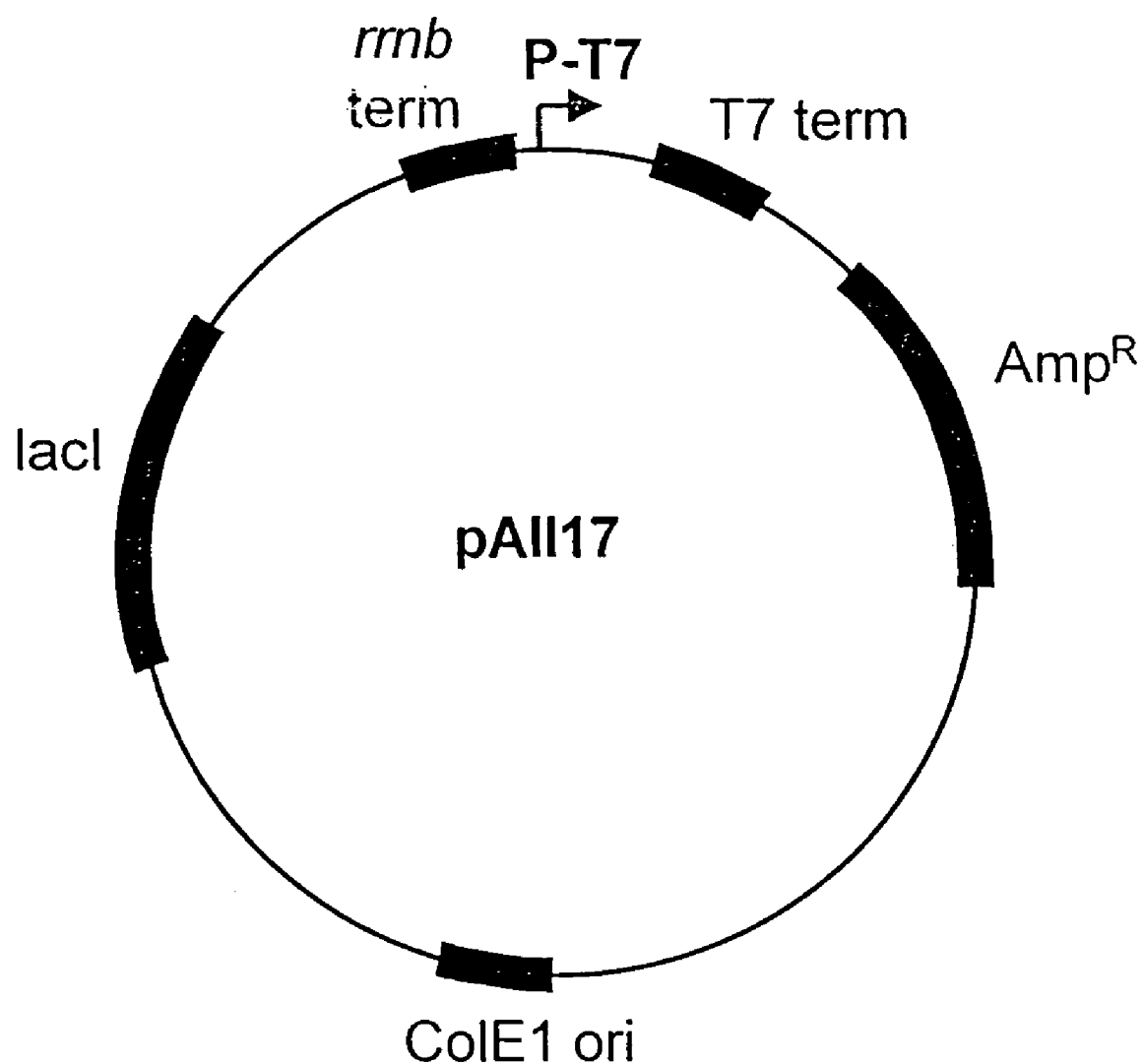
FIG. 7 shows a map of pAII17.

2) The mutagenized endonuclease gene library is prepared and cloned into an expression vector by standard techniques. The expression vector should be capable of inducible overexpression and may exhibit low-level constitutive expression of the endonuclease library. One such vector is pAGR3 (New England Biolabs, see FIG. 6) containing a Ptac promoter, the lacI$^q$ gene, a four-fold repeat of the rrnb transcription terminator upstream of the promoter, a Co/E1 origin of replication and an ampicillin resistance gene. Other suitable expression vectors may contain an IPTG-inducible promoter (Plac, Ptac, Ptrc), or a T7 promoter. Examples of suitable T7 vectors include pET21a, pET21at (a pET21a derivative constructed at New England Biolabs where 4 copies of the rrnb transcription terminator are inserted upstream of the T7 promoter) and pAII17 (New England Biolabs, see FIG. 7). When such T7 vectors are employed, protein overexpression occurs in a bacterial strain carrying the T7 RNA polymerase gene normally regulated by lacI. (e.g. ER2744 [fhuA2 lacZ::T7 gene1 glnV44 e14-rfbD1? relA1? endA1 spoT1? thi-1 Δ(mcrC-mrr)114::IS10] or ER2848 [F' proA+B+ lacI$^q$ Δ(lacZ)M15 zzf::Tn10(TetR) fhuA2 lacZ::T7gene1 glnV44 e14-rfbD1? relA1? endA1 spoT1? thi-1 Δ(mcrC-mrr)114::IS10] New England Biolabs). However, other inducible expression systems and prokaryotic hosts may be substituted.

3) The mutagenized endonuclease library may be introduced into a bacterial strain pre-modified with a non-cognate pattern of DNA methylation. Preferably, pre-modification consists of transforming a bacterial strain with one or more plasmids carrying a methylase gene and subsequently preparing those cells for transformation of the endonuclease library. For example, ER2502 ([fhuA2 ara-14 leu Δ(gpt-proA)62 lacY1 glnV44 galK2 rpsL20 endA1 R(zgb210::Tn10)Tet S xyl-5 mtl-1 Δ(mcrC-mrr)HB101] New England Biolabs) may be used when using a vector with an IPTG-inducible promoter; although, any strain may be used so long as it is tolerant of the imposed DNA methylation state and it is capable of efficient chemical transformation and electroporation. Other suitable strains include, but are not limited to, JM107, HB101, NM522, ER1821, ER2267, ER2744 and ER2848. When employing a vector with a T7 promoter, ER2744 and ER2848 are preferred due to the presence of an IPTG-inducible T7 RNA polymerase gene. Upon endonuclease library introduction, surviving strains are selected on Luria-Bertani (LB) agar plates containing the inducer molecule, an antibiotic to select the endonuclease plasmid and an antibiotic to ensure maintenance of the methylase plasmid(s).

4) Surviving colonies are pooled and plasmid DNA is prepared from the cells. The methylase plasmids are destroyed by digestion with at least two restriction enzymes. The pooled endonuclease library DNA is introduced into a DNA damage indicator strain, for example, ER1992 (NEB#907), which contains the dinD1:lacZ gene fusion (U.S. Pat. No. 5,498,535). Other DNA damage indicator strains may be substituted for the above where the reporter gene is fused to a promoter induced by the SOS repair response. Other DNA damage-inducing promoters which can be used include dinA (Iwasaki, et al., *J. Bacteriol.* 172:6268–6273 (1990)) and dinG (Lewis, *J. Bacteriol,* 174:5110–5116 (1992)). Other indicator/reporter genes which can be fused to any of the above promoters include alkaline phosphatase (phoA) (Hoffman and Wright, *Proc. Natl. Acad. Sci. USA,* 82:5107–5111 (1985)), luciferase (lux) (Engelrecht, *Science* 227:1345–1347 (1985)), β-glucuronidase (Metcalfe, *Gene,* 129:17–25 (1993)), aminoglycoside phosphotransferase (Ward, et al., *Mol. Gen. Genet,* 203:468–478 (1986)), and endoglucanase (Bingle, et al., *Can. J. Microbiol.,* 39:70–80 (1993)). Where the lac Z reporter gene system is utilized, transformants are selected at a predetermined temperature (for example 30° C.–42° C.) on agar plates containing an antibiotic to select for the endonuclease plasmid and X-gal to serve as the substrate for blue color development upon induction of the SOS response and expression of the dinD1::lacZ gene fusion. Blue cells are presumed to be carrying active endonuclease variants that survived the first selection in the presence of the non-cognate pattern of DNA methylation.

5) Cells determined to be carrying the active restriction endonuclease gene are selected and cultured in order to isolate a minimal amount of plasmid DNA for a subsequent transformation. Alternatively, indicator colonies that are positive for active endonuclease are pooled and plasmid DNA is prepared without culturing in order to maintain the integrity of active clones.

6) The endonuclease clones derived from indicator colonies that are positive are transformed into the DNA damage indicator strain now carrying the same methylase plasmid(s) as in step 3 to provide the same pattern of methylation protection as in the first genetic selection. For example, transformed cells are plated on LB-agar containing the indicator substrate, an antibiotic to select the endonuclease plasmid and an antibiotic to maintain the methylase plasmid(s). If the non-cognate pattern of methylation protects the cellular DNA from variant endonuclease cleavage, then the indicator response for colonies that are positive for the active endonuclease will not be induced and colonies that are negative will result. For example, the emergence of white colonies of a dinD1::lacZ strain suggests that the endonuclease variant displays cleavage preference towards the recognition sequence(s) protected by the non-cognate methylase(s).

7) To further analyze the novel endonuclease, aliquots of individual colonies may be taken for plasmid DNA isolation and sequencing. In one embodiment, the aliquots are taken from white colonies cultured at 30°–37° C. for 6–16 hours. The remaining cells may be lysed and the resulting extract analyzed for endonuclease activity and specificity towards an appropriate DNA substrate. The DNA substrate should allow distinction between restriction of the original recognition sequence(s) and a preference for the desired recognition sequence(s).

8) Endonuclease variants displaying a preference for the desired recognition sequence(s) may be sequenced to identify those genetic changes and amino acid substitutions responsible for alteration of the enzyme specificity/recognition site preference.

9) Those skilled in the art of protein engineering will be able to evaluate the importance of each of the genetic changes present in the selected clones and use this information to rationally design improved endonuclease variants with desired enzymatic properties. The mutations responsible for alteration of enzyme specificity are identified by inference and/or site-directed mutagenesis. The mutations deemed important for altering substrate specificity are combined into one endonuclease clone with the objective of creating a superior endonuclease variant. This variant or variants selected directly from one round can be mutagenized further and subjected to a subsequent round of selection(s) until the desired variant is isolated. At any point in the process, the skilled artisan may choose to make site-directed changes to the endonuclease gene in order to maximize the efficiency of the selection process.

The references referred to above and below are hereby incorporated by reference herein.

The following Examples are provided to aid in the understanding of embodiments of the invention and are not intended as a limitation thereof.

EXAMPLE 1

Alteration of BstYI Performance to 5'-AGATCT-3' Specificity by Random Mutagenesis, Genetic Selection and Site-Directed Mutagenesis The endonuclease BstYI recognizes and cleaves all hexanucleotide sequences described by 5'-RGATCY-3' with similar proficiency. In this Example, the genetic selection method of the present invention was applied to isolate one or more BstYI variants with cleavage preference towards AGATCT. The sequence AGATCT (FIG. 1B) was methylated at the N4 position of cytosine by the BglII N4-cytosine methyltransferase (Brooks and Roberts, *Nucleic Acids Res.* 10:913–934 (1982), Erlich, et al., *J. Bac.* 169:939–943 (1987)). Methylation of the N4 position of cytosine is known to inhibit cleavage of the AGATCT DNA sequence by BstYI. The BglII methylase gene (bglIIM) from *Bacillus globigii* (ATCC 49670) was isolated from pUC-BglIIM (Anton, et al., *Gene* 187:19–27 (1997)) by BamHI digestion and subsequently filled-in with Klenow fragment to produce blunt ends. The blunt-ended bglIIM fragment was ligated into SmaI-digested/CIP-treated pSYX20 (Morgan, et al., *Gene* 183:215–218 (1996)). This clone, pSYX-BglIIM, was employed during the genetic selection procedure to provide methylation protection where indicated.

The BstYI endonuclease gene (bstYIR) was amplified from pET21at-BstYIR (U.S. Pat. No. 6,403,354 B1) by error-prone PCR (Leung, et al., *Technique* 1:11–15 (1989), Cadwell and Joyce, *PCR Methods Applic.* 2:28–33 (1992)). Two sets of PCR conditions were selected to give two levels of mutagenesis of the bstYIR gene (Shafikhani, et al., *Biotechniques* 23:304–310 (1997)) resulting in mutagenic libraries A1 and A2.

A1 PCR conditions were as follows: 8 ng plasmid template per 100 µl reaction, 0.4 µM forward and reverse primers, 5U Taq DNA polymerase, 7 mM MgSO$_4$, 0.15 mM MnCl$_2$, 0.2 mM dATP, 0.2 mM dGTP, 1.0 mM dCTP, 1.0 mM dTTP, 10 mM KCl, 10 mM (NH$_4$)SO$_4$, 20 mM Tris-HCl (pH 8.8@ 25° C.) and 0.1% Triton X-100. Thermocycling parameters were: 1 cycle for 3 min@94°; 15 cycles (1 min@94° C., 1 min@50° C., 1 min@72° C.) and 1 cycle for 7 min@72° C. A Perkin-Elmer 2400 thermocycler was used for all PCR reactions. A2 PCR conditions were exactly as A1 conditions except 30 cycles of amplification were used. Sequencing the 612 bp bstYIR gene of genetically selected clones revealed an average of 5 nucleotide substitutions within the A1 mutagenic library and 11 nucleotide substitutions within the A2 mutagenic library. No frameshift mutations were observed in any of the sequenced clones. However, the majority of clones contained a stop codon, presumably allowing the BstYI variants to be tolerated in the presence of a non-cognate pattern of methylation. The amber stop codon TAG was found disproportionately, explaining why endonuclease activity was detected in each of the clones as this stop codon is suppressed to a significant degree due to the glnV44 locus present in both selection strains ER2502 (NEB#1149; New England Biolabs, Inc., Beverly, Mass.) and ER1992 (NEB#907; New England Biolabs, Inc., Beverly, Mass.). The glnV44 locus is responsible for glutamine incorporation at UAG via expression of a suppressor tRNA$^{Gln}$ molecule. The mutagenized bstYIR gene libraries A1 and A2 were digested with XbaI/XhoI and each were ligated into 50 ng XbaI/SalI-digested, CIP-treated pAGR3 to create expression vector libraries pAGR3BstYIR-A1 and pAGR3BstYIR-A2. Ligation was carried out for 16 hours at 16° C. followed by heat-denaturing the ligase for 30 min at 65° C. The 20 µl ligation reactions were drop-dialyzed against de-ionized water for 4 hours. Then 10% of each reaction was mixed with 40 µL ER2502 [pSYX-BglIIM] cells prepared for electroporation (BioRad Gene Pulser II protocol). The cell/DNA mix was electroporated at 1.8 kV in a 0.1 cm cuvette (BioRad) followed by addition of 1.0 ml SOC media. The cell suspension was incubated at 37° C. for 1 hour and plated (160 µl×6 plates) on LB-agar containing 100 µg/ml ampicillin, 15 µg/ml tetracycline and 0.3 mM IPTG. The plates were incubated 16 hours at 37° C. and survivors on each plate were pooled by LB broth resuspension and plasmid DNA was prepared from the cells on each plate. The plasmid DNA from each plate was digested with BamHI, SpeI and SalI to eliminate pSYX-BglIIM from each library. After heat denaturation of the restriction enzymes (20 min, 80° C.), an aliquot of each digestion mix was transformed into 20 µl ER1992, the DNA damage indicator strain. Each transformation mix was plated on 4 LB-agar plates containing 100 µg/ml ampicillin and 40 µg/ml X-gal. Clones from the A1 expression library produced 4–8 dark blue colonies per plate while clones from the A2 expression library produced 1–4 dark blue colonies per plate. These individual dark blue colonies were cultured at 30° C. for 3 hours in LB and Amp and plasmid DNA was prepared from each culture. The individual DNA preparations were transformed into ER1992 chemically-competent cells carrying pSYX-BglIIM. The transformations were plated on LB-agar containing Amp, Tet and X-gal and incubated for 16 hours at 37° C. Individual white colonies were cultured at 37° C., induced with 0.5 mM IPTG for 3 hours and assayed for endonuclease activity and preference for cleavage of AGATCT. The activity/specificity assay was conducted as follows:

Ten milliliters of induced culture were pelleted and the supernatant was removed. The cell pellet was resuspended in 1.0 ml sonication buffer: 10 mM Tris-HCl (pH 7.5@25° C.), 10 mM β-mercaptoethanol, 0.1 mM EDTA. The cell suspension was sonicated twice for 25 sec using an Ultrasonics, Inc. Cell Disruptor. The cell debris was pelleted for 10 min at 14,000 rpm. Two microliters of the resulting extract was added to the following 25 μl DNA cleavage reaction: 0.5 μg pUCAdenoXba substrate, 1×NEB BstYI buffer (10 mM Tris-HCl (pH 7.9@25° C.), 10 mM MgCl$_2$, 1 mM dithiothreitol), 0.1 mg/ml BSA. The substrate pUCAdenoXba (New England Biolabs, Inc., Beverly, Mass.) consists of an Adenovirus-2 DNA fragment from XbaI site 10,579 to XbaI site 30,455 cloned into the XbaI site of pUC19. The circular substrate is 22,562 bp and contains 18 BstYI sites, 4 BglII sites and 4 BamHI sites. As demonstrated in FIG. 3 (lanes 4 and 9), the digestion patterns of BstYI and BglII are distinctly different. Of 45 selected clones, 2 BstYI variants displayed a digestion pattern indicating a preference for cleavage of AGATCT. The amino acid substitutions of clone 9 were R2opal/K49R/K87R/K133N. (R2opal=Arginine codon at position 2 changed to the TGA stop codon. Tryptophan is inserted at UGA at a low frequency by the tryptophan-specific tRNA.) The amino acid substitutions of clone A1c were Q28H/S172amber/Y176C. (S172amber=Serine codon at position 172 changed to the TAG stop codon). Assuming that glutamine was being incorporated by amber suppression, the codon at position 172 of clone A1c was changed to CAG and the clone was renamed clone 121. Site-directed mutagenesis of the wild-type bstYIR gene determined that the substitutions of K133N and S172Q or S172N are responsible for alternation of BstYI specificity. The two substitutions, K133N and S172N, were combined in one BstYI variant that was designated NN1.

NN1 was purified from strain ER2744 [pET21at-NN1, pACYC-BstYIM, pCEF8] in the following manner: 500 ml cells induced with 0.5 mM IPTG for 3 hours at 37° C. were pelleted and the supernatant was removed. The cell pellet was resuspended in 10 ml sonication buffer: 10 mM Tris-HCl (pH 7.5@25° C.), 10 mM β-mercaptoethanol, 0.1 mM EDTA. The cell suspension was sonicated 6 times for 25 sec. After sonication, 25 mM NaCl was added and the cell extract was heated at 65° C. for 30 min to denature E. coli proteins. The heated extract was centrifuged at 15,000 rpm for 30 minutes and the clarified supernatant was retained. Glycerol was added to a final concentration of 5% before loading the supernatant onto a Heparin-Sepharose FF column equilibrated with 10 mM Tris-HCl (pH 7.5@25° C.), 25 mM NaCl, 10 mM β-mercaptoethanol, 0.1 mM EDTA and 5% glycerol. Fractions were eluted with a 0.025–0.8 M NaCl gradient. Fractions containing >90% endonuclease as determined by SDS-PAGE analysis were pooled and the NaCl concentration was adjusted to 0.3 M. The pooled fractions were allowed to flow through a DEAE-Sepharose column to accomplish DNA/RNA removal. The DEAE-Sepharose column was pre-equilibrated with 10 mM Tris-HCl (pH 7.5@25° C.), 0.3 M NaCl, 10 mM β-mercaptoethanol, 0.1 mM EDTA and 5% glycerol. The DEAE flow-through was dialyzed overnight at 4° C. in 20 mM Tris-HCl (pH 7.5@25° C.), 100 mM KCl, 10 mM β-mercaptoethanol, 0.1 mM EDTA and 5% glycerol. Glycerol was added to a final concentration of 50% and the purified protein was stored at −20° C. NN1 displays an even greater preference for cleavage of AGATCT than clones 9 or 121 and purified NN1 protein maintains the same thermostability as wild-type BstYI.

Figure 3:
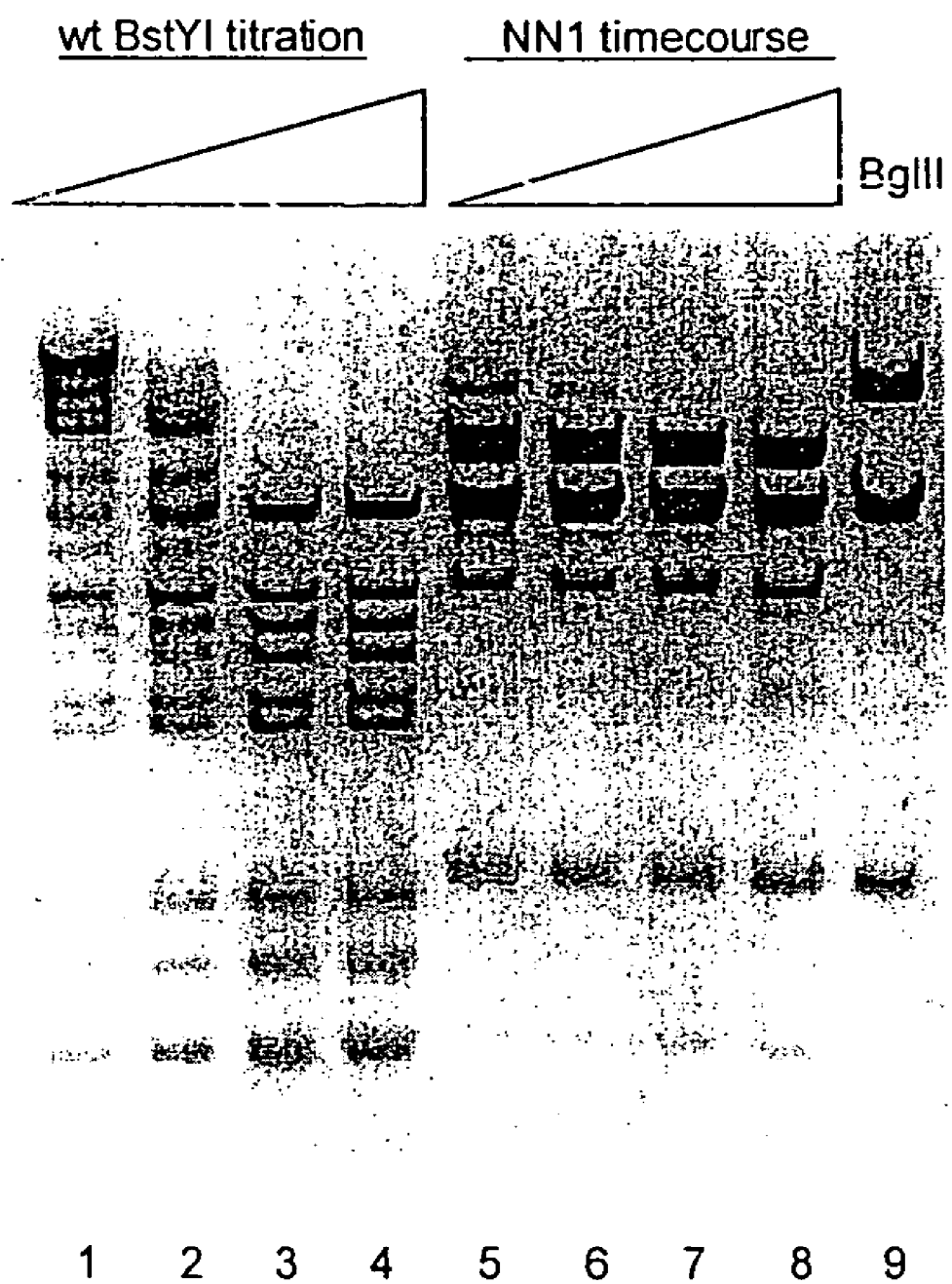
FIG. 3 is the DNA cleavage pattern of clone NN1 vs. wild-type BstYI assayed on 0.5 µg substrate pUCAdenoXba. Lanes 1–4 represent cleavage with 0.5, 1.0, 2.0 and 4.0 units wild-type BstYI for 1 hour, respectively. Lanes 5–9 represent cleavage with an excess of clone NN1 for 30, 60, 90 and 120 min, respectively. Lane 9 is complete digestion of 0.5 µg pUCAdenoXba with Bg/II to show the pattern of restriction at 5'-AGATCT-3' only. All reactions were incubated at 55° C.

By combining the genetic selection method of the present invention, interpretation of the selected genetic alterations by a skilled artisan and site-directed mutagenesis, a BstYI variant was isolated that preferentially recognizes and cleaves 5'-AGATCT-3' (FIGS. 3 and 4). NN1 displays a 7-fold preference for recognition and cleavage of 5'-AGATCT-3' relative to 5'-AGATCC-3' or 5'-GGATCT-3' and recognition and cleavage of the 5'-GGATCC-3' (SEQ ID NO:6) site is not detected. (Relative amounts of cleavage were calculated by quantifying the rate of product formation displayed in FIG. 4).

EXAMPLE 2

Selection of NotI Variants with Altered Specificity for DNA Recognition and Cleavage The recognition sequence of NotI is 5'-GCGGCCGC-3'. Restriction endonucleases with 8-bp recognition sites are rarely found in nature. Therefore, development of such enzymes by protein engineering is of considerable commercial interest. The method of the present invention is especially suited for this type of endeavor since an extensive range of DNA methylases are available that will modify derivations of the wild-type NotI recognition sequence. However, randomly choosing a non-cognate methylase to employ in the genetic selection of NotI variants imposes an unfair bias on the evolution process. Instead, a preliminary study was conducted to isolate a NotI variant with relaxed specificity. This work was modeled after a study of EcoRI substrate specificity where important amino acid residues were identified using a DNA-damage indicator strain expressing the cognate EcoRI methylase (Heitman and Model, EMBO J. 9:3369–3378 (1990)). In the case of the NotI study, the EagI methylase served as the "cognate" methylase since it modifies the sequence 5'-NCGGCCGN-3' and protects the host genomic DNA from cleavage by wild-type NotI.

I. Isolation of NotI variant 44-2A

Figure 5:
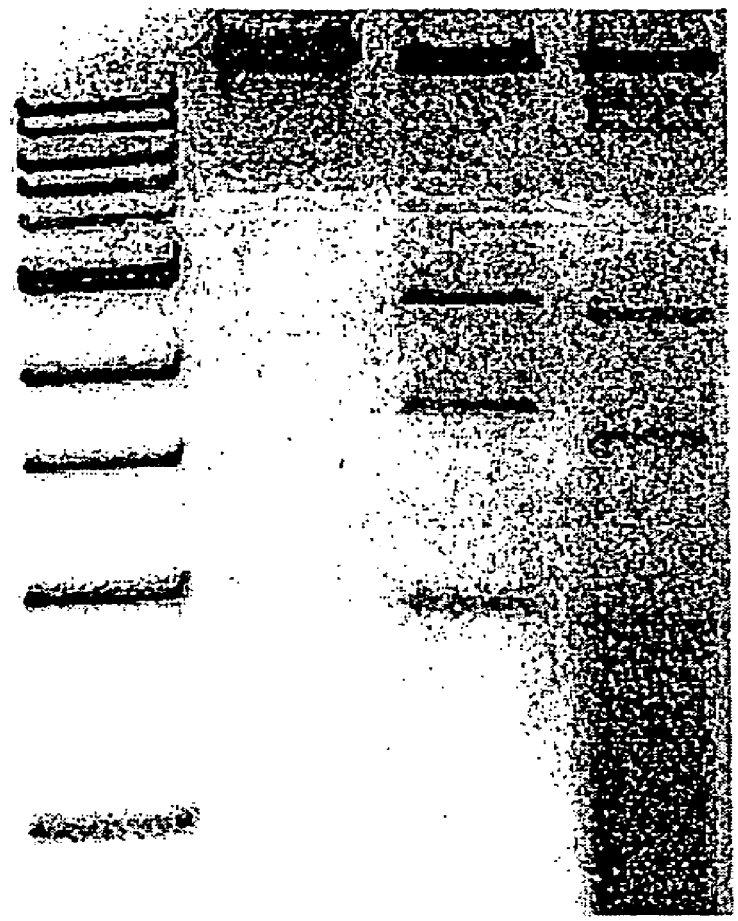
FIG. 5 shows an agarose gel where U=uncut substrate pXba, NotI=pXba cut With NotI and 44-2A=pXba cut by mutant 44-2A. (Star: 16kb fragment cut into 9kb and 7kb fragment).

The EagI methylase clone (pACYC184EagIM) was isolated from the NotI overproduction strain (NEB #816 and U.S. Pat. No. 5,371,006) and transformed into DNA-damage indicator strain ER1992. The wild-type notIR gene was subjected to error-prone PCR mutagenesis with the following conditions: 10 ng plasmid template pAII17-NotIR, 0.4 μM T7 promoter and T7 terminator primers, 5U Taq DNA polymerase, 7 mM MgSO$_4$, 0.2 mM dATP, 0.2 mM dGTP, 1.0 mM dCTP, 1.0 mM dTTP, 10 mM KCl, 10 mM (NH$_4$)SO$_4$, 20 mM Tris-HCl (pH 8.8@25° C.) and 0.1% Triton X-100. Thermocycling parameters were 1 cycle for 3 min@94° C., 25 cycles (1 min@94° C., 1 min@50° C., 1 min @72° C.) and 1 cycle for 7 min@72° C. The PCR product was digested with XbaI and SalI, gel-purified and cloned into pAGR3. The pAGR3 mutagenic library was transformed into ER1992 [pACYC184EagIM] cells by electroporation and plated on LB-agar containing 100 μg/μL ampicillin, 33 μg/μL chloramphenicol and 80 μg/μL X-gal. Of approximately 60,000 transformants, 10 blue colonies were isolated. The endonuclease clones present within these colonies were amplified by colony PCR and cloned into T7 expression vector pAII17. The substrate specificity of each clone was analyzed by overexpression within ER2744 carrying pACYC188-EagIM and pSYX20-HhaIM. The cellular extract of clone 44-2A produced an alternate cleavage pattern when incubated with substrate pUCAdenoXba (previously linearized by PmeI). Specifically, the 16,748 bp fragment produced by wild-type NotI was partially digested into 7 kb and 9 kb fragments (see FIG. 5). Inspection of the substrate sequence determined that cleavage at 5'-GCAGCTGC-3' and/or 5'-GCTGCAGC-3' may be responsible for production of the alternate restriction fragments.

DNA sequencing of clone 44-2A revealed nucleotide substitutions that result in the amino acid substitutions P9S, E156K and I201T. We deduced that the relaxed specificity was at least partially caused by the E156K substitution, as this variant could not be isolated in host ER2744 [pACYC-EagIM, pSYX20-HhaIM] (due to cell toxicity). Subsequently, the E-156K substitution was isolated in an allele that contained an amber codon at position 37 as a means of attenuation. The Amb37/E156K allele was expressed from pAGR3 in ER1992 [pACYC184-EagIM] and the resulting extract produced the same altered pattern of digestion as the original clone, 44-2A, thus confirming the importance of substitution E156K for relaxation of substrate specificity.

The altered substrate specificity of E156K was investigated in vivo by expressing the BbvI methylase in addition to the EagI methylase. The BbvI methylase modifies the C5 position of the first cytosine in the sequence 5'-GCAGC-3' and 5'-GCTGC-3'. Therefore, modification of 5'-GCAGCTGC-3' and 5'-GCTGCAGC-3' by BbvI methylase is predicted to protect DNA from cleavage by a variant NotI (REBASE: http://rebase.neb.com). In fact, modification of the genomic DNA by the BbvI methylase increased the tolerance of host ER2744 to Amb37/E156K expressed from pAGR3. When plated on LB-agar containing increasing levels of IPTG, loss of cell viability was detected at 80 μM IPTG in the presence of BbvI and EagI methylation; whereas, viability was lost at 25 μM IPTG when the host was protected by EagI methylation only. This rapid in vivo test serves to give an indication of the altered specificity and aids in the choice of the appropriate methylase to be employed in the genetic selection of the present invention.

II. Genetic Selection of NotI Variants Possessing 5'-GCWGCWGC-3' Specificity

The "relaxed" NotI variant Amb37/E156K can be subjected to one or more rounds of genetic selection in order to isolate an endonuclease that preferentially recognizes 5'-GCWGCWGC-3' (where W=A or T).

In round one, a mutagenized Amb37/E156K library is ligated into pAGR3 and the resulting clones transformed into ER2744 protected by only the BbvI methylase. The appropriate amount of IPTG in selection one is determined by testing which level results in an adequate number of "active" survivors as revealed in selection two by the indicator strain ER1992. Active clones from selection two are transformed into ER1992 expressing the BbvI methylase. White or light-blue colonies in step three are cultured, cell extract is prepared and the endonuclease activity is analyzed in vitro by incubation with an appropriate DNA substrate. Clones displaying an even greater preference for 5'-GCWGCWGC-3' as compared to the parent are sequenced and the responsible amino acid alterations are determined by inference and/or site-directed mutagenesis. The most desired variant(s) are subjected to a second round of genetic selection and so forth. In each subsequent round it is important to increase the in vivo selection pressure imposed on the mutagenized gene library. In this example, the level of IPTG can be incrementally increased in each round and/or codon 37 can be restored to CAG thus significantly increasing the in vivo DNA-damaging effects of those variants possessing activity outside the spectrum of BbvI methylation. Finally, the desired NotI clone will be sequenced to determine the genetic alterations and the protein will be over-expressed, purified to near homogeneity and characterized in detail.

EXAMPLE 3

Selection of Endonuclease Variants with an Alternate Specificity for DNA Cleavage The genetic selection method of the present invention can be applied to engineer an existing endonuclease to recognize and cleave an alternate DNA sequence. As outlined in FIG. 1A, an element of the genetic selection procedure is methylation protection of the host genomic DNA by one or more non-cognate DNA methyltransferase. The imposed DNA methylation pattern specifically protects the desired, alternate sequence(s) while allowing the cognate DNA sequence(s) to be efficiently cleaved by the wild-type endonuclease. This critical element can be verified by in vivo and in vitro studies of the non-cognate DNA methyltransferase(s) and the wild-type endonuclease. Regardless of the temperature optimum of the wild-type endonuclease, the activity of the starting mutagenic library can be attenuated to maximize the efficiency of the genetic selection process. Options include creating an amber codon within the open reading frame, creating an opal codon within the open reading frame, changing the start codon to GTG or mutating the RBS sequence to decrease the translational efficiency. In addition, the use of a T7 expression vector is especially advantageous for achieving low-level constitutive expression of the endonuclease library in a DNA-damage reporter strain that does not carry a T7 RNA polymerase gene. For example, the mutagenic library for round one can be cloned into the T7 expression vector pAII17. Mutagenesis of the endonuclease gene can be accomplished by error-prone PCR conditions "A1" as described in Example 1. After error-prone PCR amplification, the mutagenic library (Rgene*) is digested with the appropriate restriction enzymes, ligated into pAII17 and subjected to the following genetic selections:

SELECTION 1—The mutagenic library is introduced into strain 1 by electroporation or transformation of chemically-competent cells. Strain 1 (e.g., ER2744 [pACYC-Mgene]) will have been pre-modified with the desired, non-cognate pattern of methylation. Survivors can be selected at 25° C.–42° C. on LB-agar plates containing a low-level of IPTG (0–100 μM), Amp and an antibiotic to ensure maintenance of the methylase plasmid(s). Surviving colonies from each plate are pooled and plasmid DNA is prepared from each pool. The methylase plasmid(s) is destroyed by digestion with multiple restriction enzymes.

SELECTION 2—The mutagenic endonuclease sub-libraries are transformed into DNA-damage indicator strain such as ER1992 and plated at 30° C.–42° C. on LB-agar containing Amp and X-gal. Individual active clones displaying a dark blue colony phenotype are cultured for 2–16 hours at 30° C.–42° C. and plasmid DNA is prepared form these cultures.

SELECTION 3—Individual clones can be transformed into ER1992 [pACYC-Mgene] which has been pre-modified with the same pattern of methylation as in strain 1/selection 1. The transformants can be plated at 30° C.–42° C. on Amp, X-gal and an antibiotic to maintain the methylase plasmid(s). Individual white colonies are cultured, induced with IPTG and cell extract is prepared. Alteration of endonuclease specificity can be analyzed by adding the cell extract to an in vitro DNA cleavage reaction containing a substrate which allows distinction between restriction of the original recognition sequence(s) and a preference for the desired recognition sequence(s). Endonuclease variants displaying the desired specificity (or partial alteration of specificity) are sequenced and the responsible mutations are determined by inference and/or site-directed mutagenesis. The mutations responsible for alteration of specificity can be combined in one endonuclease clone by site-directed mutagenesis. This clone, or any of the variants selected directly from round one, can be chosen for further improvement by a subsequent round of genetic selections. During selection 1 of round two, the IPTG level will be increased as compared to round one in order to increase the selection pressure. This will increase the likelihood of eliminating those clones with only a partial alteration of substrate specificity. The selection process can end after round two or can proceed for multiple rounds until the desired endonuclease variant is isolated. With each subsequent round, selection 1 will be made more stringent, preferably by increasing the level of IPTG present in the agar plates. Finally, the desired endonuclease clone will be sequenced to determine the genetic alterations and the protein will be over-expressed, purified to near homogeneity and characterized in detail.

What is claimed is:

1. A method for altering an endonuclease recognition site specificity, comprising:

(a) subjecting a mutagenized endonuclease gene library to a genetic selection in a population of prokaryotic host cells expressing one or more non-cognate DNA methyltransferases, wherein the genetic selection selects for viable cells in the population; and (b) identifying whether the viable cells express an active mutated endonuclease with an altered recognition site specificity.

2. A method according to claim 1, wherein the mutagenized endonuclease gene library is formed by: error prone PCR, chemical mutagenesis, assembly PCR, DNA shuffling, in vivo mutagenesis, cassette mutagenesis, recursive ensemble mutagenesis or exponential ensemble mutagenesis.

3. A method according to claim 1, wherein the endonuclease activity is attenuated.

4. A method according to claim 3, wherein attenuating the activity of the endonuclease expressed by the mutagenized endonuclease gene library is achieved by modifying the mutagenized endonuclease gene library using modification means selected from: creating an amber codon within the open reading frame; creating an opal codon within the open reading frame; changing the start codon to GTG or TTG; mutating the ribozyme binding site (BRS) sequence or utilizing a T7 expression vector wherein the host cell is T7 RNA polymerase negative.

5. A method according to claim 1, wherein step (b) comprises: pooling viable prokaryotic host cells; isolating from the host cells, plasmid DNA encoding mutagenized endonuclease genes from the library; and transforming the plasmid DNA into a population of indicator cells for detecting DNA damage.

6. A method according to claim 5, wherein the mutagenized endonuclease genes are subjected to repeated genetic selections in the population of host cells of claim 1 and in the population of indicator cells.

7. A method according to claim 6, wherein the genetic selection in the population of indicator cells comprises a first population of indicator cells lacking a non-cognate methylase(s) and a second population of indicator cells expressing the non-cognate methylase(s).

8. A method according to claim 1, wherein altered recognition-site specificity comprises: relaxed recognition-site specificity, increased recognition-site specificity or alternate recognition-site specificity.

9. A method according to claim 1, further comprising determining a sequence for the recognition site for the endonuclease.

10. A method for altering recognition site specificity of an endonuclease, comprising:
   (a) creating a mutagenized endonuclease gene expression plasmid library from a target endonuclease gene and transforming prokaryotic cells with the mutagenized library, wherein the prokaryotic cells express one or more non-cognate methyltransferases;
   (b) selecting prokaryotic cells which are viable after transformation and isolating plasmid DNA from the viable cells;
   (c) determining whether the isolated plasmid DNA encodes an active endonuclease by transforming the plasmid DNA into DNA-damage indicator cells;
   (d) screening the plasmid DNA encoding the active endonuclease for altered specificity; and
   (e) optionally repeating steps (a) through (d) to obtain the endonuclease with altered recognition-site specificity.

11. A method according to claim 10, further comprising: determining the altered recognition site for the endonuclease.

12. A method according to claims 1 or 10 wherein the endonuclease is BstYI.

13. A method according to claims 1 or 10 wherein the endonuclease is NotI.

14. A method according to claim 12, wherein the recognition site specificity is altered from 5'-RGATCY-3' to 5'-AGATCT-3'.

15. A endonuclease having an altered recognition site specificity wherein the specificity is altered according to claim 1 or claim 10.

16. A modified BstYI enzyme, having a preferred recognition site specificity of 5'-AGATCT-3'.

17. A method for modifying recognition site specificity of an endonuclease from a parent specificity to a target specificity, comprising:
   (a) obtaining a sequence for a plurality of mutated endonucleases obtained according to any of the methods of claims 1 or 10 to determine the mutation(s) for each mutated endonuclease; and
   (b) mutating a gene encoding the endonuclease to produce one or more of the mutations identified in step (a) so as to produce an endonuclease with the target specificity.

* * * * *

UNITED STATES PATENT AND TRADEMARK OFFICE
CERTIFICATE OF CORRECTION

| | | |
|---|---|---|
| PATENT NO. | : 7,052,897 B2 | Page 1 of 1 |
| APPLICATION NO. | : 10/501196 | |
| DATED | : May 30, 2006 | |
| INVENTOR(S) | : James C. Samuelson et al. | |

It is certified that error appears in the above-identified patent and that said Letters Patent is hereby corrected as shown below:

At column 18, claim number 4, line number 65, delete "(BRS)" and insert -- (RBS) --, therefor.

Signed and Sealed this

Seventeenth Day of May, 2011

David J. Kappos
*Director of the United States Patent and Trademark Office*

SEQUENCE LISTING

<160> NUMBER OF SEQ ID NOS: 2

<210> SEQ ID NO 1
<211> LENGTH: 612
<212> TYPE: DNA
<213> ORGANISM: Bacillus stearothermophilus Y406
<220> FEATURE:
<221> NAME/KEY: CDS
<222> LOCATION: (1)..(612)
<223> OTHER INFORMATION:

<400> SEQUENCE: 1

```
atg aga att gtt gaa gta tat tcg cat ttg aac ggg ttg gaa tac ata      48
Met Arg Ile Val Glu Val Tyr Ser His Leu Asn Gly Leu Glu Tyr Ile
1               5                   10                  15 caa gtt cac ttg cca cat att tgg gaa gaa att caa gaa att att gtt      96
Gln Val His Leu Pro His Ile Trp Glu Glu Ile Gln Glu Ile Ile Val
                20                  25                  30 tct att gac gca gaa gct tgt aga acg aag gaa tca aaa gaa aag aca    144
Ser Ile Asp Ala Glu Ala Cys Arg Thr Lys Glu Ser Lys Glu Lys Thr
            35                  40                  45 aaa caa gga caa ata ctt tat agt ccc gta gct tta aat gaa gca ttc    192
Lys Gln Gly Gln Ile Leu Tyr Ser Pro Val Ala Leu Asn Glu Ala Phe
        50                  55                  60 aag gaa aaa tta gaa gca aaa ggt tgg aaa gaa agt cga aca aac tat    240
Lys Glu Lys Leu Glu Ala Lys Gly Trp Lys Glu Ser Arg Thr Asn Tyr
65                  70                  75                  80 tat gtg act gct gac cca aag ctg att cgt gaa aca tta tca ctt gaa    288
Tyr Val Thr Ala Asp Pro Lys Leu Ile Arg Glu Thr Leu Ser Leu Glu
                85                  90                  95 cca gag gaa caa aag aaa gtg att gaa gcc gca gga aaa gaa gca tta    336
Pro Glu Glu Gln Lys Lys Val Ile Glu Ala Ala Gly Lys Glu Ala Leu
            100                 105                 110 aag tct tat aat caa acg gat ttt gta aaa gat aga gtg gca ata gaa    384
Lys Ser Tyr Asn Gln Thr Asp Phe Val Lys Asp Arg Val Ala Ile Glu
        115                 120                 125 gtt caa ttc gga aaa tat tct ttt gtc gct tat gac ctt ttc gtc aaa    432
Val Gln Phe Gly Lys Tyr Ser Phe Val Ala Tyr Asp Leu Phe Val Lys
    130                 135                 140 cac atg gct ttc tat gtt agt gat aaa att gac gtt ggt gtc gaa ata    480
His Met Ala Phe Tyr Val Ser Asp Lys Ile Asp Val Gly Val Glu Ile
145                 150                 155                 160 ttg cca atg aag gaa tta tca aaa gaa atg tct tcg gga atc agt tat    528
```

-continued

```
Leu Pro Met Lys Glu Leu Ser Lys Glu Met Ser Ser Gly Ile Ser Tyr
            165                 170                 175 tac gaa ggt gaa tta tac aat gtg ata cgg caa ggt cgt ggc gtt cct    576
Tyr Glu Gly Glu Leu Tyr Asn Val Ile Arg Gln Gly Arg Gly Val Pro
            180                 185                 190 gcc gtt ccg ttg gtt tta atc ggg att gcc cct taa                    612
Ala Val Pro Leu Val Leu Ile Gly Ile Ala Pro
            195                 200
```

<210> SEQ ID NO 2
<211> LENGTH: 203
<212> TYPE: PRT
<213> ORGANISM: Bacillus stearothermophilus Y406

<400> SEQUENCE: 2

```
Met Arg Ile Val Glu Val Tyr Ser His Leu Asn Gly Leu Glu Tyr Ile
1               5                   10                  15

Gln Val His Leu Pro His Ile Trp Glu Glu Ile Gln Glu Ile Ile Val
            20                  25                  30

Ser Ile Asp Ala Glu Ala Cys Arg Thr Lys Glu Ser Lys Glu Lys Thr
            35                  40                  45

Lys Gln Gly Gln Ile Leu Tyr Ser Pro Val Ala Leu Asn Glu Ala Phe
    50                  55                  60

Lys Glu Lys Leu Glu Ala Lys Gly Trp Lys Glu Ser Arg Thr Asn Tyr
65                  70                  75                  80

Tyr Val Thr Ala Asp Pro Lys Leu Ile Arg Glu Thr Leu Ser Leu Glu
            85                  90                  95

Pro Glu Glu Gln Lys Lys Val Ile Glu Ala Ala Gly Lys Glu Ala Leu
            100                 105                 110

Lys Ser Tyr Asn Gln Thr Asp Phe Val Lys Asp Arg Val Ala Ile Glu
            115                 120                 125

Val Gln Phe Gly Lys Tyr Ser Phe Val Ala Tyr Asp Leu Phe Val Lys
    130                 135                 140

His Met Ala Phe Tyr Val Ser Asp Lys Ile Asp Val Gly Val Glu Ile
145                 150                 155                 160

Leu Pro Met Lys Glu Leu Ser Lys Glu Met Ser Ser Gly Ile Ser Tyr
            165                 170                 175

Tyr Glu Gly Glu Leu Tyr Asn Val Ile Arg Gln Gly Arg Gly Val Pro
            180                 185                 190

Ala Val Pro Leu Val Leu Ile Gly Ile Ala Pro
            195                 200
```